(12) United States Patent
Lechmann et al.

(10) Patent No.: US 8,012,208 B2
(45) Date of Patent: Sep. 6, 2011

(54) IMPLANT FOR INTERVERTEBRAL SPACE

(75) Inventors: Beat Lechmann, Bettlach (CH); Robert Frigg, Bettlach (CH); Roger Bürki, Balsthal (CH)

(73) Assignee: Synthes USA, LLC, West Chester, PA (US)

( * ) Notice: Subject to any disclaimer, the term of this patent is extended or adjusted under 35 U.S.C. 154(b) by 1577 days.

(21) Appl. No.: 11/318,937

(22) Filed: Dec. 22, 2005

(65) Prior Publication Data
US 2006/0195190 A1 Aug. 31, 2006

Related U.S. Application Data

(63) Continuation of application No. PCT/CH03/00412, filed on Jun. 24, 2003.

(51) Int. Cl.
*A61F 2/44* (2006.01)
(52) U.S. Cl. .................................................. 623/17.11
(58) Field of Classification Search ..... 623/17.11–17.16
See application file for complete search history.

(56) References Cited

U.S. PATENT DOCUMENTS

| | | | |
|---|---|---|---|
| 4,834,757 A | | 5/1989 | Brantigan |
| 5,425,772 A | * | 6/1995 | Brantigan ................... 623/17.11 |
| 5,456,723 A | * | 10/1995 | Steinemann et al. ...... 623/23.53 |
| 5,888,224 A | | 3/1999 | Beckers et al. |
| 6,258,125 B1 | * | 7/2001 | Paul et al. .................. 623/17.11 |
| 6,699,288 B2 | | 3/2004 | Moret |
| 7,442,211 B2 | * | 10/2008 | de Villiers et al. ......... 623/17.14 |
| 2001/0020186 A1 | * | 9/2001 | Boyce et al. ............... 623/17.16 |

FOREIGN PATENT DOCUMENTS

| | | |
|---|---|---|
| FR | 2 764 795 | 12/1998 |
| FR | 2 816 201 | 5/2002 |
| WO | WO 95/08306 | 3/1995 |
| WO | WO 00/25707 | 5/2000 |
| WO | WO 00/45753 | 8/2000 |

* cited by examiner

*Primary Examiner* — Anu Ramana
(74) *Attorney, Agent, or Firm* — Stroock & Stroock & Lavan LLP

(57) ABSTRACT

An implant for an intervertebral space with a shaped body. The implant has a top contact surface to be placed on a base plate of a body of the vertebra adjoining the implant from above, a bottom contact surface to be placed on a cover plate of a body of the vertebra adjoining the implant from below, two lateral surfaces, a front lateral and a rear lateral surface as well as a central axis that intersects the two contact surfaces, a longitudinal axis that intersects the front and rear lateral surfaces and a transverse axis that intersects the lateral surfaces. The implant also has a central plane situated between the contact surfaces and at right angles to the central axis of the body. The contact surfaces have a plurality of macroscopic teeth with central axes, where the central axes of the plurality of teeth are inclined relative to the central plane in such a manner, that a rotation of the body of 90° about the longitudinal axis is facilitated in one direction and impeded in the other direction. The distance between the two lateral surfaces is smaller than the distance between the two contact surfaces.

37 Claims, 5 Drawing Sheets

IMPLANT FOR INTERVERTEBRAL SPACE

CROSS REFERENCE TO RELATED APPLICATION

This application is a continuation of International Patent Application No. PCT/CH2003/000412, filed Jun. 24, 2003, the entire contents of which is expressly incorporated herein by reference.

TECHNICAL FIELD

The present invention relates generally to implants for intervertebral spaces.

BACKGROUND OF THE INVENTION

It is well known in the art to use intervertebral implants in a posterior lumbar fusion of two adjoining bodies of the vertebra. WO 95/08306 to Beckers describes such an implant for an intervertebral space. The Beckers implant comprises a body with a flat lens-shaped profile having convex surfaces. The convex surfaces are positioned on the superior and inferior, respectively, surfaces of the adjoining bodies of the vertebra, so that the greatest part of the profile of the implant coincides with the biconcave shape of the sagittal interface of the intervertebral space. In the other two planes, the body has parallel flat sides. Furthermore, an opening passes through the body parallel to its central axis, i.e. from one contact surface to the other one, so that the body can be filled with bony substance. The roundings (round edges) at the front of the body, as well as the convex contact surfaces, do not require any mechanical machining, for example milling or chiseling of the superior and inferior, respectively, surfaces of the adjoining bodies of the vertebra. The cross-sectional surface, that is perpendicular to the longitudinal axis, has two roundings, which are executed on diagonally situated corners, so that the implant can be introduced into the intervertebral space transversely, i.e., with its contact surfaces transverse to the longitudinal axis of the vertebra. Following insertion, the implant is rotated 90° with a suitable tool until the contact surfaces of the body come into contact with the superior and inferior, respectively, surfaces of the adjoining bodies of the vertebra. A disadvantage of the Beckers implant is that the contact surfaces can have a structure, with ribs extending either parallel to the longitudinal axis or transverse to it. By virtue of this structure, with teeth having symmetrical flanks, either the introduction of the implant into the intervertebral space as well as its slipping out is equally facilitated or made difficult, and the rotation of the body is equally prevented or made difficult in both directions.

Another known intervertebral implant is disclosed in U.S. Pat. No. 4,834,757 to Brantigan. The Brantigan intervertebral implant comprises a frame-like body, that has an asymmetric structure on the contact surfaces as well as on both lateral surfaces, whereby this structure comprises saw-tooth like teeth, the flanks of which are directed against the front end of the body and consequently push both adjoining bodies of the vertebra apart during the introduction of the implant into the intervertebral space. Whereas, the steep flanks hook in and thus prevent a slipping out of the implant. A disadvantage of this implant is that the teeth make rotation of the implant difficult in both directions.

SUMMARY OF THE INVENTION

The present invention is to provide a remedy for the above-discussed disadvantages. It is an object of the invention to produce an implant for an intervertebral space that makes rotation of the implant about the longitudinal axis of the body possible in one direction and prevents it in the opposite direction.

The present invention accomplishes the objective set out above with an intervertebral implant. The implant has an essentially cuboid-shaped body. The implant also has a top contact surface to be placed on a base plate of a body of the vertebra adjoining the implant from above, a bottom contact surface to be placed on a cover plate of a body of the vertebra adjoining the implant from below, two lateral surfaces, a front lateral and a rear lateral surface as well as a central axis that intersects the two contact surfaces, a longitudinal axis that intersects the front and rear lateral surfaces and a transverse axis that intersects the lateral surfaces. The implant also has a central plane situated between the contact surfaces and at right angles to the central axis of the body. The contact surfaces have a plurality of macroscopic teeth with central axes, where the central axes of the plurality of teeth are inclined relative to the central plane in such a manner, such that rotation of the body about the longitudinal axis is facilitated in one direction and impeded in the other direction. The distance between the two lateral surfaces is smaller than the distance between the two contact surfaces.

The advantages achieved by the invention are essentially that by virtue of the implant according to the invention implanting is possible by simply inserting and rotating the implant. An undesirable shifting, in particular a slipping out of the implant from the intervertebral space can be prevented, as well as an undesirable reverse rotation of the implant in the intervertebral space can be prevented. Lateral slipping of the implant within the intervertebral space, particularly towards the centre of the bodies of the vertebra, may also be prevented.

In a preferred embodiment the macroscopic teeth are constructed so that in sectional planes they extend perpendicularly to the longitudinal axis of the body, and their central axes are inclined relative the central plane of the body.

In a further embodiment, the teeth are constructed such that their central axes are inclined also in the sectional planes through the body, which are perpendicular to the transversal axis, so that a preferred direction of shifting can be achieved, thus facilitating the introduction of the implant into the intervertebral space, whereas the implant slipping out is prevented.

The teeth are preferably constructed as inclined pyramids or inclined tapers, inclined truncated pyramids or inclined truncated tapers.

In another embodiment, the teeth are constructed so that their central axes are parallel at least on one contact surface. Preferably, however, the teeth are so constructed, that their central axes are parallel on each of the two contact surfaces.

In yet another embodiment, the teeth are so constructed that in the sectional planes, extending perpendicularly to the longitudinal axis, their central axes include an angle $+\phi$ on the top contact surface and an angle $-\phi$ on the bottom contact surface. The result of this is the advantage, that the rotation of the implant about its longitudinal axis is facilitated in one direction, whereas the rotation is considerably impeded in the other direction.

The height of the teeth relative to the relevant contact surfaces is preferably between 0.15 mm and 1.5 mm.

In a further embodiment, in two sectional planes, which are at right angle to one another and are perpendicular to the central axis, the teeth have a steep and a shallow flank each. Thus the teeth are essentially constructed as inclined pyramids, due to which a reverse rotation as well as a lateral movement of the implanted implant can be prevented.

According to yet another embodiment, the implant is made from an X-ray permeable material, that can be chosen, for example, from the following group: (a) polyaryl etherketone (PAEK), polyetherimide (PEI), polyoxymethylene (POM), liquid crystal polymer (LCP), polymethyl pentene (PMP), polysulfone (PSU), polyethersulfone (PESU or PES), polyethylene terephthalate (PETP), polymethyl methacrylate (PMMA) or ultrahigh-molecular polyethylene (UHMW-PE); and (b) polymers, which are reinforced with long or short fibers of, for example, carbon. By producing the implant from an X-ray permeable material an advantage is realized in that the surgeon or the radiologist can follow better the restructuring of the bone.

In another embodiment, the surface of the implant is roughened, achieving advantages in the behavior of the bone adhesion. The surface roughness is preferably between 2 µm and 10 µm. Experience indicates, that the bone cells grow best on the surface of the implant in this range of surface roughness.

In yet another embodiment, when viewed in sectional planes which are perpendicular to the transversal axis, the shallow flanks of the teeth enclose with a straight line that is parallel to the central axis of the body an angle $\alpha$ between 30° and 80°, while the steep flanks enclose with the same straight line an angle $\beta$ between 5° and 30°.

In a further embodiment, when viewed in sectional planes which are perpendicular to the longitudinal axis, the shallow flanks of the teeth on the top contact surface enclose with a straight line that is parallel to the central axis of the body an angle $\gamma$ between +30° and +80°, while the steep flanks enclose with the central axis of the body an angle $\delta$ between +50 and +30°. On the bottom contact surface the angle $\gamma$ is between −30° and −80° and the angle $\delta$ between −5° and −30°.

The flank angles of the teeth listed above are advantageous to secure the teeth in the end plates of the adjoining bodies of the vertebra.

The angles $\alpha$ and $\gamma$ of the shallow flanks as well as the angles $\beta$ and $\delta$ of the steep flanks are preferably the same, so that the resistance of the teeth against turning out or moving is at optimum.

The geometry of the teeth is preferably such that the volume V of a projection is between 0.15 mm$^3$ and 1.2 mm$^3$. Preferably the entire contact surfaces are covered by teeth.

In a further embodiment, the steep flanks of the teeth are provided in parallel planes. By virtue of this, an optimum resistance against turning out or moving of the implant can be achieved.

According to yet another embodiment, the essentially cuboid-shaped body is constructed in such a manner, that the second cross-sectional surface, which is perpendicular to the longitudinal axis, is rectangular and has a unilateral rounding (round edge). The advantage of this construction is that the implant can be rotated only in one direction and the contact surface, situated on the side opposite to that provided with the rounding, can be used to fit further teeth. Consequently, the number of teeth can be still kept high.

In another embodiment, the radius of the rounding is to be so dimensioned, that the contact surface to the bone is reduced by the rounding by less than half, preferably by less than a third, so that the number of teeth on the contact surfaces can be kept high.

In yet another embodiment, the essentially cuboid-shaped body is constructed in such a manner that the second cross-sectional surface, which is perpendicular to the longitudinal axis, is rectangular and has two diagonally positioned rounding. Thus the manual rotation of the implant during the operation is facilitated.

In a further embodiment, the radii of the two roundings are so dimensioned that the second cross-sectional surface of the body is reduced by less than half, preferably by less than one quarter. The advantage of this construction is that notwithstanding the roundings a high structural strength for the implant can be realized, i.e. as little as possible material is eliminated to realize the roundings.

In yet another embodiment, the roundings have an elliptical shape. The elliptical shape allows a simple start for the rotation of the implant. The resistance to rotation builds up during the rotation so that in the final position the resistance against a reverse rotation is at its maximum.

In another embodiment, the roundings have two different radii. By virtue of the larger radius, joining the lateral surfaces, the rotation of the implant is simplified at the start. By virtue of the adjoining smaller radius, joining the contact surfaces, the resistance to rotation is increased, so that in the final position the resistance to reverse rotation is at its maximum.

In still a further embodiment, the body, which has a first and a second lateral surface which intersect the contact surfaces as well as the front lateral surface, has preferably roundings arranged between the first lateral surface and the top contact surface as well as between the second lateral surface and the bottom contact surface.

In yet another embodiment, the body has second roundings, which are arranged between the front lateral surface, intersecting the contact surfaces, and the contact surfaces. The advantage of these second roundings is, that in contrast to sharp edges, the bony structure of the adjoining body of the vertebra will not get damaged. In addition, during the introduction of the implant into the intervertebral space the roundings facilitate the shifting of the implant and prevent it from getting stuck.

In a further embodiment, the implant comprises at least one, but preferably a plurality of X-ray markers. This provides the advantage, that the position and orientation of the implant in the intervertebral space is visible in X-ray pictures during the operation and post-operatively. The number of X-ray markers is between one and six, depending on the application of the implant.

In yet another further embodiment, the body has at least one bore, so that the X-ray marker, constructed as a pin, can be pressed into the bore. The pin is made from an X-ray impermeable material. Preferably the at least one bore is so arranged in the implant, that its axis is parallel to the central axis and is situated in a plane extending through the central axis and the longitudinal axis.

In another embodiment, the at least one pin has at least one radially protruding protuberance arranged circumferentially and axially centrally, and is plastically deformed when pushed into the bore, so that the pin is secured in the bore by means of a press fit.

In yet another embodiment, the pin is made from a metal, preferably steel, titanium, tantalum or gold.

Other objectives and advantages in addition to those discussed above will become apparent to those skilled in the art during the course of the description of a preferred embodiment of the invention which follows. In the description, reference is made to accompanying drawings, which form a part thereof, and which illustrate an example of the invention. Such example, however, is not exhaustive of the various embodiments of the invention, and therefore, reference is made to the claims that follow the description for determining the scope of the invention.

BRIEF DESCRIPTION OF THE DRAWINGS

The implant for the intervertebral space is explained in even greater detail in the following exemplary drawings. The intervertebral implant may be better understood by reference to the following drawings, wherein like references numerals represent like elements. The drawings are merely exemplary to illustrate the structure, operation and method of use of the multi-mode lighter and certain features that may be used singularly or in combination with other features and the invention should not be limited to the embodiments shown.

DESCRIPTION OF THE PREFERRED EMBODIMENTS

Figure 1:
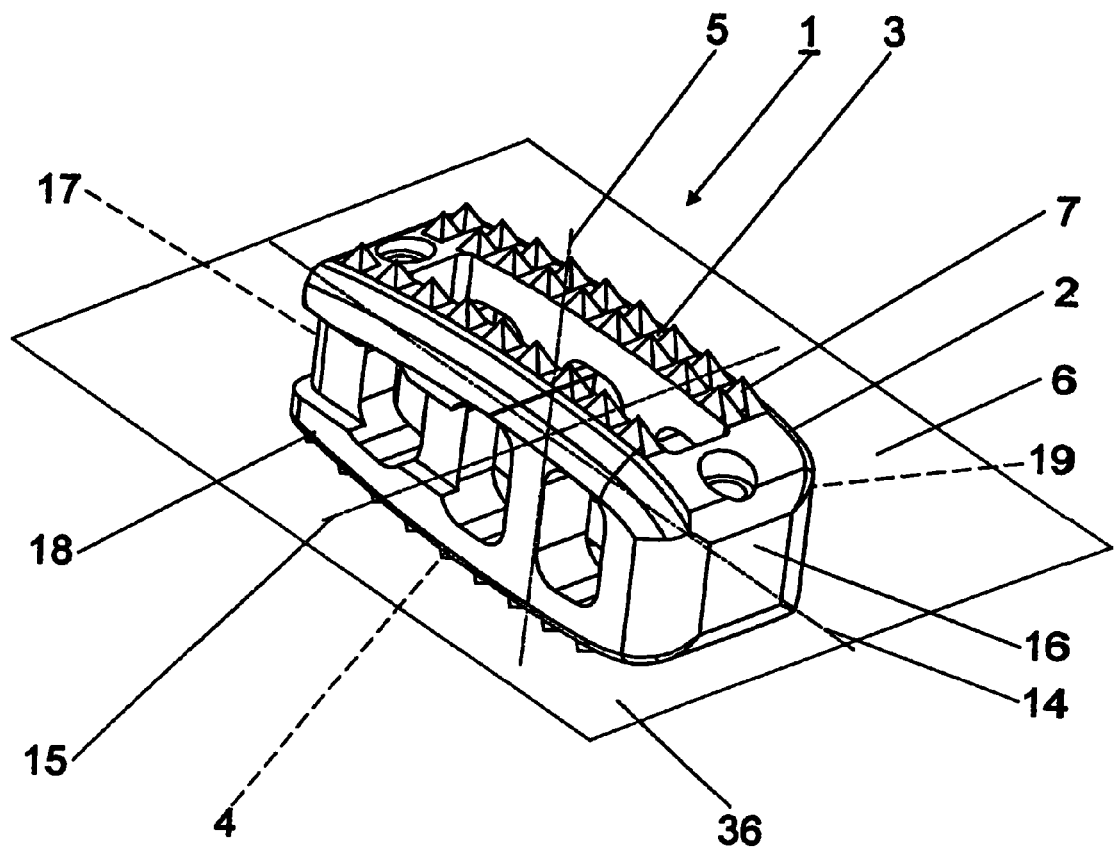
FIG. 1 shows a perspective view of an embodiment of the implant.
Figure 2:
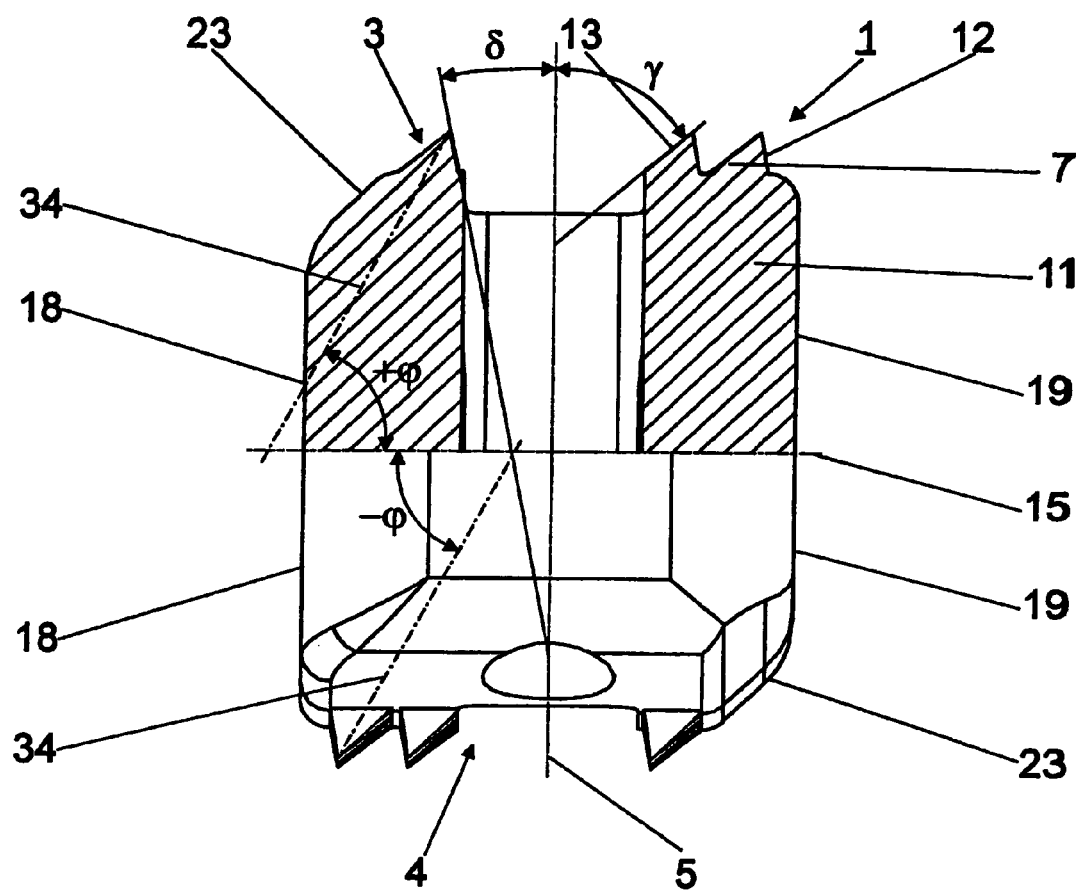
FIG. 2 shows a first cross-sectional view of the implant depicted in FIG. 1.
Figure 3:
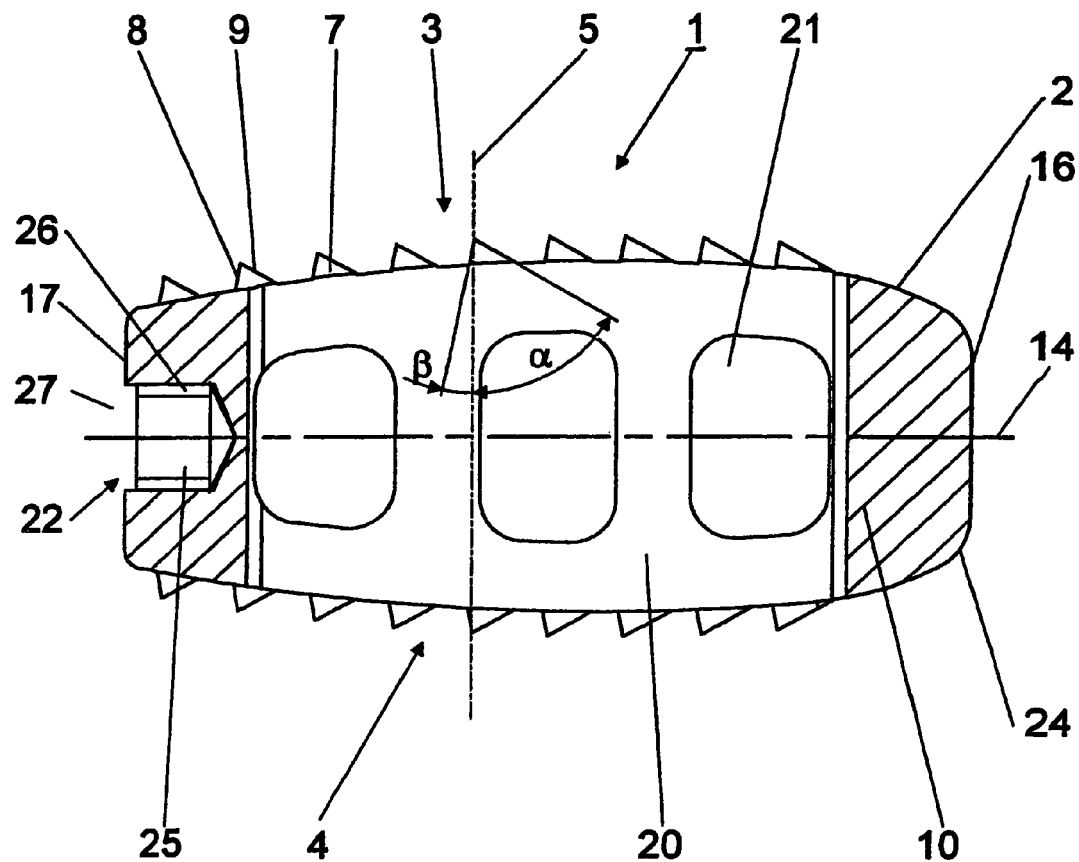
FIG. 3 shows a longitudinal sectional view of the implant of FIGS. 1 and 2, with means to accommodate a holding tool.

The implant 1, shown in FIGS. 1 to 3, consists of an essentially cuboid-shaped body 2 with top and bottom convex contact surfaces 3, 4 to be placed on the superior and inferior surface, respectively, of the two adjoining bodies of the vertebra and a central axis 5 intersecting the contact surfaces 3, 4. Two lateral surfaces 18, 19 are arranged at right angles to the contact surfaces 3, 4, as well as a front lateral surface 16 and a rear lateral surface 17. Longitudinal axis 14, which is perpendicular to the central axis 5, intersects both the front lateral surface 16 and the rear lateral surface 17. A transverse axis 15, which is also perpendicular to the central axis 5 of the body 2, intersects lateral surfaces 18, 19. The longitudinal axis 14, as well as the transverse axis 15, define a central plane 6 situated between the contact surfaces 3, 4; this plane being perpendicular to the central axis 15. The distance between the two lateral surfaces 18, 19 is smaller than the distance between the two contact surfaces 3, 4.

An opening 20, that is parallel to its central axis 5, passes through the body 2 from the top contact surface 3 to the bottom contact surface 4. Three perforations 21, parallel to the transverse axis 15, pass through the body 2 from the first lateral surface 18 to the second lateral surface 19. Consequently, the body 2 has a frame-shaped construction with a central cavity, while the front and rear lateral surfaces 16, 17 do not have bores or perforations opening into the cavity. A first cross-sectional surface 10 is defined by the central axis 5 of the body and the longitudinal axis 14, the intersection line of which with the second cross-sectional surface 11, defined by the central axis 5 of the body 2 and the transverse axis 15, coincides with the central axis 5 of the body 2.

The contact surfaces 3, 4 are fitted with macroscopic teeth 7. The teeth are preferably constructed as inclined pyramids or inclined tapers, inclined truncated pyramids or inclined truncated tapers. The height of the teeth 7 relative to the relevant contact surface is preferably between 0.15 mm and 1.5 mm. The geometry of the teeth is preferably such, that the volume V of a projection is between 0.15 mm$^3$ and 1.2 mm$^3$. Preferably the entire contact surfaces are covered by teeth.

In one embodiment, the teeth 7 are constructed such that their central axes are parallel to at least one contact surface. Preferably, however, the teeth 7 are so constructed that their central axes are parallel on each of the two contact surfaces.

The central axes 34 of the teeth 7 are inclined relative to the central plane 36 of the body 2. At the same time the teeth 7 are so constructed, that on the top contact surface 3 their central axes 34 include an angle +φ in the sectional planes, which are sectioning the body 2 perpendicular to the longitudinal axis 14, and on the bottom contact surface 4 an angle −φ with the central plane 36. In the sectional planes, that are parallel to the first cross-sectional surface 10, each tooth 7 has unidirected steep and shallow flanks 8, 9 and in the sectional planes, that are parallel to the second cross-sectional surface 11, unidirected steep and shallow flanks 12, 13 for each contact surface 3, 4, whereby:

in the sectional planes, that are parallel to the first cross-sectional surface 10, the steep flanks 8 include an angle β with a straight line that is parallel to the central axis 5 of the body 2, in the sectional planes, that are parallel to the first cross-sectional surface 10, the shallow flanks 9 include an angle α with a straight line that is parallel to the central axis 5 of the body 2, in the sectional planes, that are parallel to the second cross-sectional surface 11, the steep flanks 12 on the top contact surface 3 include an angle +δ with a straight line that is parallel to the central axis 5 of the body 2 and an angle −δ on the bottom contact surface 4, and in the sectional planes, that are parallel to the second cross-sectional surface 11, the shallow flanks 13 on the top contact surface 3 include an angle +γ with a straight line that is parallel to the central axis 5 of the body 2 and an angle −γ on the bottom contact surface 4.

The steep flanks 8 on the teeth 7 of both contact surfaces 3, 4 are on the side which faces the rear lateral surface 17. In the second cross-sectional surface 11, the steep flanks 12 of the teeth on the top contact surface 3 are provided on the right side of the teeth 7 when viewed from the front lateral surface 16 parallel to the longitudinal axis 14, while the steep flanks 12 of the teeth 7 on the bottom contact surface 4, also viewed from the front lateral surface 16 parallel to the longitudinal axis 14, are provided on the left side of the teeth 7.

In the embodiment illustrated here the angles β and δ between the steep flanks 8, 12 and the straight lines, that are parallel to the central axis 5, are the same. Similarly, the angles α and γ between the shallow flanks 9, 13 and the straight lines, that are parallel to the central axis 5, are the same.

The arrangement of the steep flanks 8 in the first cross-sectional surface 10 is such, that when the implant 1 is pushed forward with its front lateral surface 16 into an intervertebral space, the superior and inferior surface, respectively, of the adjoining bodies of the vertebra are pushed apart by the shallow flanks 9 of the teeth 7, while a possible slipping out of the implanted body 2 is prevented by the steep flanks 8. Furthermore, the arrangement of the steep flanks 12 in the second cross-sectional surface 11 is such, that in the case of turning the implant 1, pushed into the intervertebral space, to the right, the superior and inferior surface of the adjoining bodies of the vertebra are pushed apart by the shallow flanks 13 of the teeth 7, whereas a turning to the left of the implanted body 2 is prevented by the steep flanks 12.

In another embodiment, when viewed in sectional planes which are perpendicular to the transversal axis, the shallow flanks of the teeth enclose with a straight line that is parallel to the central axis of the body, an angle α between 30° and 80°, while the steep flanks enclose with the same straight line an angle β between 5° and 30°.

In a further embodiment, when viewed in sectional planes which are perpendicular to the longitudinal axis, the shallow flanks of the teeth on the top contact surface enclose with a straight line that is parallel to the central axis of the body an angle γ between +30° and +80°, while the steep flanks enclose with the central axis of the body an angle δ between +5° and +30°. On the bottom contact surface the angle γ is between −30° and −80° and the angle δ between −5° and −30°.

The flank angles of the teeth listed above are advantageous to secure the teeth in the end plates of the adjoining bodies of the vertebra.

The angles α and γ of the shallow flanks as well as the angles β and δ of the steep flanks are preferably the same, so that the resistance of the teeth against turning out or moving is at optimum.

In a further embodiment, the steep flanks of the teeth are provided in parallel planes. By virtue of this, an optimum resistance against turning out or moving of the implant can be achieved.

In a further embodiment, in two sectional planes, which are at right angle to one another and are perpendicular to the central axis, the teeth 7 have a steep and a shallow flanks each. Thus, the teeth 7 are essentially constructed as inclined pyramids, due to which a reverse rotation as well as a lateral movement of the implanted implant can be prevented.

According to yet another embodiment, the essentially cuboid-shaped body is constructed in such a manner, that the second cross-sectional surface, which is perpendicular to the longitudinal axis, is rectangular and has a unilateral rounding. The advantage of this construction is that the implant can be rotated only in one direction and the contact surface, situated on the side opposite to that provided with the rounding (round edge), can be used to fit further teeth. Consequently the number of teeth can be still kept high.

To simplify turning of the implant 1 to the right during implantation, the body 2 has roundings 23 (round edges) with two different radii between the contact surfaces 3, 4 and the lateral surfaces 18, 19. The first 23 are so arranged, that in the second cross-sectional surface 11, that is perpendicular to the longitudinal axis 14, they are situated only on a diagonal, so that the roundings 23 are arranged between the top contact surface 3 and the first lateral surface 18 and between the bottom contact surface 4 and the second lateral surface 19. With regard to the teeth 7 on the two contact surfaces 3, 4 the roundings 23 are executed on the sides having the shallow flanks 9, 13. Likewise, for a simple introduction of the implant 1 into the intervertebral space, the body 2 has second roundings 24 between the contact surfaces 3, 4 and the front lateral surface 16.

In another embodiment, the radius of the rounding is to be so dimensioned, that the contact surface to the bone is reduced by the rounding by less than half, preferably by less than a third, so that the number of teeth on the contact surfaces can be kept high.

In a further embodiment, the radii of the two roundings are so dimensioned that the second cross-sectional surface of the body is reduced by less than half, preferably by less than one quarter. The advantage of this construction is that notwithstanding the roundings 23 a high structural strength for the implant can be realized, i.e., as little as possible material is eliminated to realize the roundings 23.

In a further embodiment, the radii of the two roundings 23 are so dimensioned, that the second cross-sectional surface of the body is reduced by less than half, preferably by less than one quarter. The advantage of this construction is that notwithstanding the roundings 23 a high structural strength for the implant can be realized, i.e., as little as possible material is eliminated to realize the roundings 23.

In yet another embodiment, the roundings 23 have an elliptical shape. The elliptical shape allows a simple start for the rotation of the implant. The resistance to rotation builds up during the rotation, so that in the final position the resistance against a reverse rotation is at its maximum.

In another embodiment, the roundings 23 have two different radii. By virtue of the larger radius, joining the lateral surfaces, the rotation of the implant is simplified at the start. By virtue of the adjoining smaller radius, joining the contact surfaces, the resistance to rotation is increased, so that in the final position the resistance to reverse rotation is at its maximum.

In still a further embodiment, the body 2, that has a first and a second lateral surface 18, 19 which intersect the contact surfaces 3, 4 as well as the front lateral surface 16, has preferably roundings 23 arranged between the first lateral surface and the top contact surface as well as between the second lateral surface and the bottom contact surface.

In yet another embodiment, the body 2 has second roundings 24, which are arranged between the front lateral surface 16, intersecting the contact surfaces 3, 4, and the contact surfaces. The advantage of these second roundings 24 is, that in contrast to sharp edges, the bony structure of the adjoining body of the vertebra will not get damaged. In addition, during the introduction of the implant into the intervertebral space the roundings 23 facilitate the shifting of the implant and prevent it from getting stuck.

The rear end 28 the implant 1 further comprises means 22 for a rotation-preventing accommodation of a holding tool. In the embodiment shown in FIG. 3, these means 22 to accommodate the holding tool comprise a bore 25 that is coaxial with the longitudinal axis 14 and has an inside thread 26 that penetrates into the implant 1 from the rear lateral surface 17. So that the holding tool can be joined with the implant 1 in a rotation-preventing manner, a groove 27, extending parallel to the transverse axis 15 and also executed in the rear lateral surface 17, is located in the implant 1. For a rotation-preventing joint between the holding tool and the implant 1 a segment of the holding tool, having an external thread, is screwed into the inside thread 26, and subsequently a corresponding segment is introduced into the groove 27.

In yet another embodiment, the essentially cuboid-shaped body is constructed in such a manner, that the second cross-sectional surface, which is perpendicular to the longitudinal axis, is rectangular and has two diagonally positioned rounding. Thus the manual rotation of the implant during the operation is facilitated.

The implant 1 may be made from an X-ray permeable material, that can be chosen, for example, from the following group: (a) polyaryl etherketone (PAEK), polyetherimide (PEI), polyoxymethylene (POM), liquid crystal polymer (LCP), polymethyl pentene (PMP), polysulfone (PSU), polyethersulfone (PESU or PES), polyethylene terephthalate (PETP), polymethyl methacrylate (PMMA) or ultrahigh-molecular polyethylene (UHMW-PE); and (b) polymers, which are reinforced with long or short fibres of, for example, carbon. By producing the implant from an X-ray permeable material, a surgeon or radiologis can follow better the restructuring of the bone.

In another embodiment, the surface of the implant 1 is course such that it has a rough surface allowing for better bone adhesion. The surface roughness is preferably between 2 μm and 10 μm. Experience indicates, that the bone cells grow best on the surface of the implant in this range of surface roughness.

Figure 4:
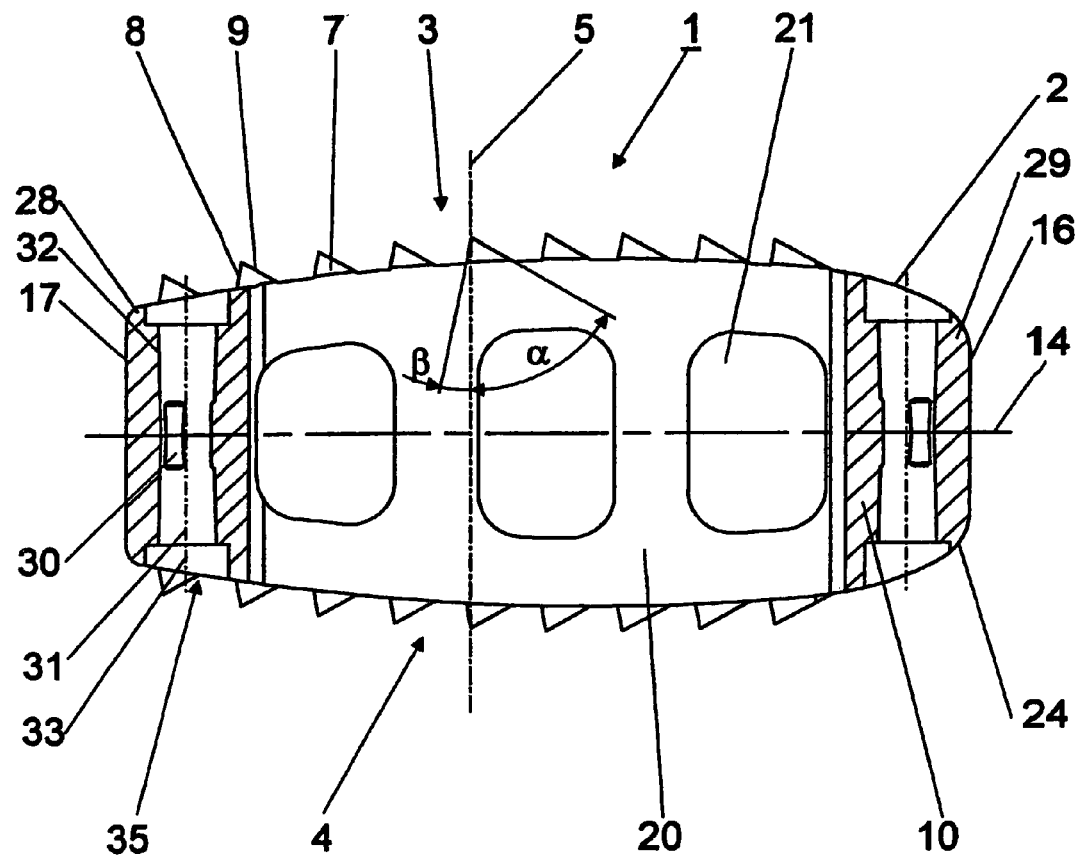
FIG. 4 shows a longitudinal sectional view of an embodiment of the implant with X-ray markers.
Figure 5:
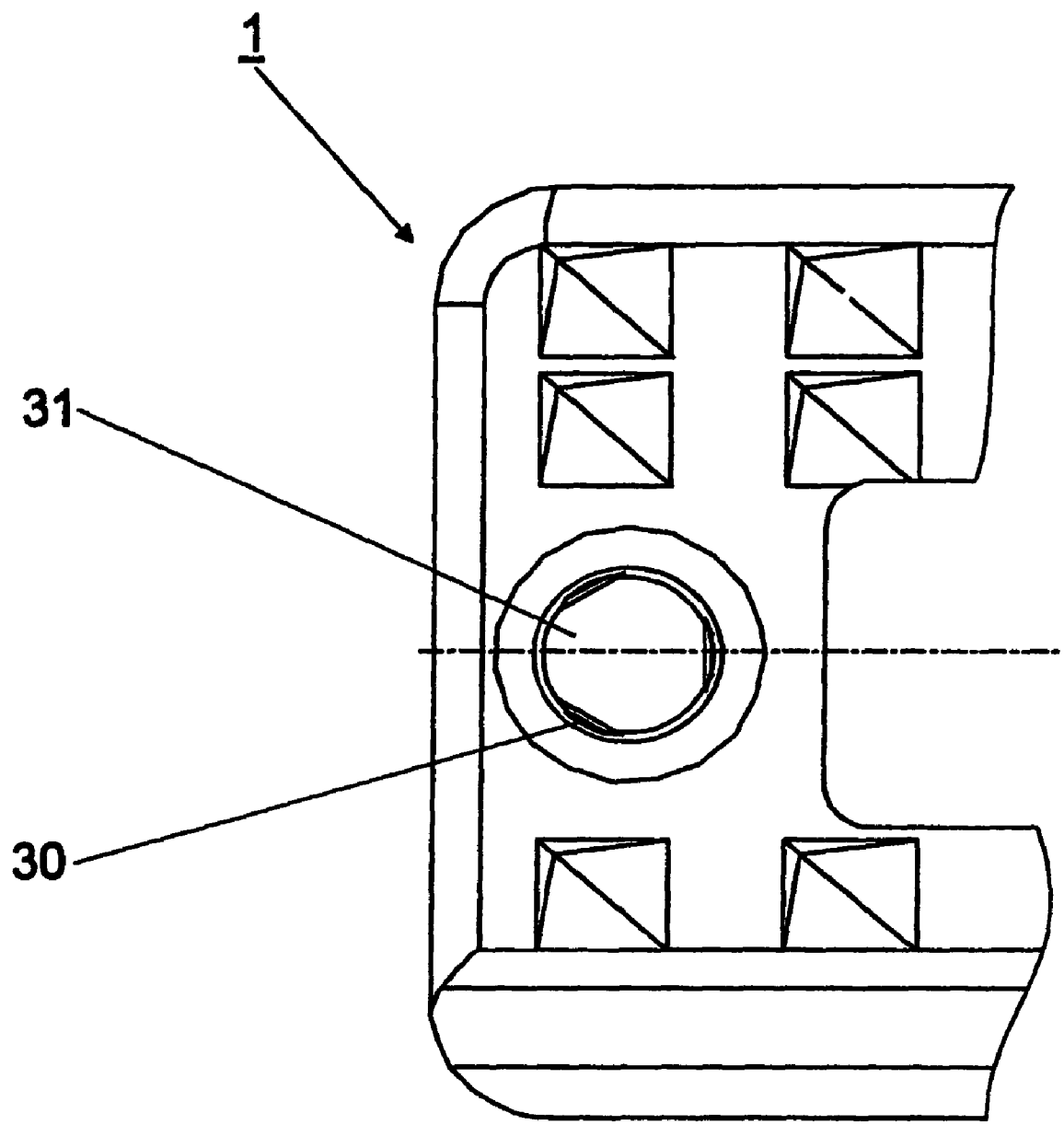
FIG. 5 shows a to view of the rear end of the implant depicted in FIG. 4.

An embodiment of the implant 1 according to the invention shown in FIGS. 4 and 5 comprises one or more X-ray markers 35. This provides the advantage, that the position and orientation of the implant in the intervertebral space is visible in X-ray pictures during the operation and post-operatively. In an advantageous manner, the number of X-ray markers is between one and six, depending on the application of the implant. These X-ray markers 35 are constructed as pins 31 which are introduced into bores 32. The pin is made from an X-ray impermeable material. Preferably the at least one bore is so arranged in the implant, that its axis 33 is parallel to the central axis and is situated in a plane extending through the central axis and the longitudinal axis. To fasten the pins 31 in the bores 32, the pins 31 have one or more protuberances 30, preferably three protuberances, each on their circumferences and preferably axially centrally. During the pressing in of the pins 31 into the bores 32 the protuberances 30 are plastically deformed, so that the pins 31 are held in the bores 32 by a press fit. In the embodiment shown here the body 2 has two bores 32, of which one bore 32 is arranged at the front end 29 of the implant 1 and the other bore 32 at the rear end 28 of the implant 1. The bores 32 are constructed so that their axes 33 are parallel to the central axis 5 and lie in a plane extending through the central axis 5 and the longitudinal axis 14.

In yet another embodiment, the pin is made from a metal, preferably steel, titanium, tantalum or gold.

The following is a description of a method of inserting the implant 1 between adjoining vertebra. So that a surgeon can advance with instruments, necessary for the operation, in the space of the disk, the adjoining facet joints and the laminae are partly removed. Following this, by means of probes, the required size of the implant 1 is determined. The implant 1, selected in this manner, is then joined with the corresponding holding tool (not illustrated), that can be fastened on the rear end 28 of the implant 1. The introduction of the implant 1 is carried out in such a manner, that the lateral surfaces 18, 19, not having teeth 7, are aligned parallel to the superior and inferior surface, respectively, of the two adjoining bodies of the vertebra. The implant 1 can be introduced into the intervertebral space through the partly removed dorsal structures of the bodies of the vertebra. After the implant 1 was introduced into the intervertebral space up to the desired depth, the surgeon rotates the implant 1 by means of the holding tool by 90° about the longitudinal axis 15, so that the contact surfaces 3, 4, provided with teeth 7, will be fixed on the superior and inferior plates. By rotating the implant 1, the surgeon achieves a traction in the anterior structures of the spinal column. By this, the lordosis, inter alia, can be restored. Finally, using the same operation steps, a second implant 1 is introduced, so that an implant 1 is provided on both sides of the spinal marrow cord.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. An implant for an intervertebral space comprising:
   a shaped body with:
   a top contact surface to be placed on an end plate of the vertebra adjoining the implant from above, a bottom contact surface to be placed on an end plate of the vertebra adjoining the implant from below;
   two lateral side surfaces having a length greater than their width, a front and a rear surface as well as a central axis that intersects the two contact surfaces, a longitudinal axis that intersects the front and rear surfaces, and a transverse axis that intersects the lateral side surfaces; and
   a central plane defined by the longitudinal axis and the transverse axis and situated between the contact surfaces and at right angles to the central axis of the body,
   wherein the contact surfaces have a plurality of teeth with central axes,
   wherein the central axes of the plurality of teeth are inclined relative to the central plane in such a manner that rotation of the body 90 degrees about the longitudinal axis is facilitated in one direction and impeded in the other direction; and
   wherein the maximum distance between the two lateral side surfaces is smaller than the maximum distance between the two contact surfaces.

2. An implant according to claim 1, wherein viewed in the planes sectioning the body perpendicularly to the longitudinal axis, the central axes of the teeth are inclined to the central plane.

3. An implant according to claim 1, wherein when viewed in the planes sectioning the body perpendicularly to the transverse axis the central axes of the teeth are inclined to the central plane.

4. An implant according to claim 1, wherein the structure of the teeth is selected from the group consisting of inclined pyramids, inclined tapers, inclined truncated pyramids, and inclined truncated tapers.

5. An implant according to claim 1, wherein when viewed in sectional planes of the body, which are perpendicular to the longitudinal axis, the central axes of the teeth on the top contact surface are at an angle of $+\phi$ with respect to the central plane and the central axes of the teeth on the bottom contact surface are at an angle $-\phi$ with respect to the central plane.

6. An implant according to claim 1, wherein the height of the teeth is between 0.15 mm and 1.5 mm.

7. An implant according to claim 1, wherein in two planes, which are at right angle to one another and are perpendicular to the central axis of the body, and each tooth of the plurality of teeth have a steep and a shallow flank each.

8. An implant according to claim 7, wherein when viewed in sectional planes which are perpendicular to the transversal axis, the shallow flanks enclose with a straight line that is parallel to the central axis of the body, an angle $\alpha$ and the steep flanks enclose with the same straight line an angle $\beta$.

9. An implant according to claim 7, wherein when viewed in sectional planes which are perpendicular to the longitudinal axis, the shallow flanks on the top contact surface enclose with a straight line that is parallel to the central axis of the body an angle $+\gamma$ and the steep flanks enclose with the same straight line an angle $+\delta$, and
   wherein when viewed in sectional planes which are perpendicular to the longitudinal axis, the shallow flanks on the bottom contact surface enclose with a straight line that is parallel to the central axis of the body an angle $-\gamma$ and the steep flanks enclose with the same straight line an angle $-\delta$.

10. An implant according to claim 9, wherein the Angles $\alpha$ and $\gamma$ of the shallow flanks are the same.

11. An implant according to claim 9, wherein the angles β and δ of the steep flanks are the same.

12. An implant according to claims 9, wherein the angles α and γ of the shallow flanks are between 30 degrees and 80 degrees.

13. An implant according to claim 9, wherein the angles β and δ of the steep flanks are between 5 degrees and 30 degrees.

14. An implant according to claim 7, wherein the steep flanks of the teeth are situated in parallel planes.

15. An implant according to claim 1, wherein the implant is made from an X-ray permeable material.

16. An implant according to claim 1, wherein the surface of the implant is roughened.

17. An implant according to claim 16, wherein the surface roughness is between 2 μm and 10 μm.

18. An implant according to claim 1, wherein the volume V of a tooth is between 0.15 mm$^3$ and 1.2 mm$^3$.

19. An implant according to claim 1, wherein when viewed in a cross-sectional surface, which is contained in a plane perpendicular to the longitudinal axis, the body has a rectangular construction with a unilateral rounding to facilitate rotation of the body about the longitudinal axis in the facilitated direction.

20. An implant according to claim 19, wherein the radius of the rounding is so dimensioned, that the contact surface to the bone is reduced by the rounding by less than a third.

21. An implant according to claim 1, wherein when viewed in a cross-sectional surface, which is contained in a plane perpendicular to the longitudinal axis, the body has a rectangular construction with two diagonally provided roundings to facilitate rotation of the body about the longitudinal axis in the facilitated direction.

22. An implant according to claim 21, wherein the radii of the two roundings are so dimensioned, that the second cross-sectional surface of the body is reduced by less than one quarter.

23. An implant according to claim 21, wherein the roundings are elliptical.

24. An implant according to claim 21, wherein the roundings have two different radii.

25. An implant according to claim 1, wherein the two lateral surfaces intersect the contact surfaces as well as the front surface, and that diagonally between a first lateral surface and the top contact surface as well as between a second lateral surface and the bottom contact surface the body has rounded edges to facilitate rotation of the body about the longitudinal axis in the facilitated direction.

26. An implant according to claim 1, wherein the body has a roundings between the front surface and the contact surfaces where the front surface intersects the contact surfaces.

27. An implant according to claim 1, wherein the implant has at least one X-ray marker.

28. An implant according to claim 27, wherein the implant has a plurality of X-ray markers.

29. An implant according to claim 27, wherein the body has at least one bore and the X-ray marker comprises a pin that can be pressed into the bore and is made from an X-ray impermeable material.

30. An implant according to claim 29, wherein at least one bore has an axis, that is parallel to the central axis and is situated in a plane extending through the central axis and the longitudinal axis.

31. An implant according to claim 29, wherein the pin comprises at least one protuberance protruding radially and arranged circumferentially on the pin.

32. An implant according to claim 29, wherein the pin is made from a metal, preferably from steel, titanium, tantalum or gold.

33. An implant according to claim 1, wherein the entire contact surfaces are covered by teeth.

34. An implant for an intervertebral space comprising:
a shaped body with:
a top contact surface to be placed on an end plate of the vertebra adjoining the implant from above, a bottom contact surface to be placed on an end plate of the vertebra adjoining the implant from below;
two lateral side surfaces having a length greater than their width, a front and a rear surface as well as a central axis that intersects the two contact surfaces, a longitudinal axis that intersects the front and rear surfaces, and a transverse axis that intersects the lateral side surfaces; and
a central plane situated between the contact surfaces and at right angles to the central axis of the body,
wherein the contact surfaces have a plurality of teeth with central axes,
wherein the central axes of the plurality of teeth are inclined relative to the central plane in such a manner that rotation of the body 90 degrees about the longitudinal axis is facilitated in one direction and impeded in the other direction;
wherein the body has rounded edges with two different radii between the contact surfaces and the lateral side surfaces; and
wherein the maximum distance between the two lateral side surfaces is smaller than the maximum distance between the two contact surfaces.

35. An implant according to claim 34, wherein the implant has first rounded edges are arranged in a cross-sectional surface, contained in a plane perpendicular to the longitudinal axis, the first rounded edges positioned between the top contact surface and the first lateral side surface and between the bottom contact surface and the second lateral side, the first rounded edges having the same radii.

36. An implant according to claim 35, wherein the implant has a substantially rectangular cross section and said first rounded edges are located diagonally opposite each other.

37. An implant according to claim 35, wherein when viewed in sectional planes of the body perpendicular to the longitudinal axis, the central axes of the teeth on the top surface are at an angle +φ with respect to the central plane and the central axes of the teeth on the bottom surface are of an angle −φ with respect to the central plane.

* * * * *